US008483399B2

(12) United States Patent
Shou

(10) Patent No.: US 8,483,399 B2

(45) Date of Patent: Jul. 9, 2013

(54) CONDENSER MICROPHONE, MICROPHONE UNIT, AND BLOOD PRESSURE GAUGE

(75) Inventor: Tokurin Shou, Shibukawa (JP)

(73) Assignee: Japan Precision Instruments Inc., Shibukawa-shi (JP)

(*) Notice: Subject to any disclaimer, the term of this patent is extended or adjusted under 35 U.S.C. 154(b) by 1387 days.

(21) Appl. No.: 11/907,681

(22) Filed: Oct. 16, 2007

(65) Prior Publication Data

US 2008/0089527 A1 Apr. 17, 2008

(30) Foreign Application Priority Data

Oct. 16, 2006 (JP) ................................ 2006-281962

(51) Int. Cl.
*A61B 7/04* (2006.01)
*H04R 1/46* (2006.01)

(52) U.S. Cl.
USPC ............................ 381/67; 381/71.7; 600/493

(58) Field of Classification Search
USPC ........................................ 381/67, 71.1, 71.7
See application file for complete search history.

(56) References Cited

U.S. PATENT DOCUMENTS

| | | | | | |
|---|---|---|---|---|---|
| 3,963,881 | A | * | 6/1976 | Fraim et al. | 381/357 |
| 4,105,020 | A | * | 8/1978 | Matsuoka et al. | 600/495 |
| 4,181,122 | A | * | 1/1980 | Ueda | 600/493 |
| 4,837,833 | A | * | 6/1989 | Madaffari | 381/322 |
| 4,887,693 | A | * | 12/1989 | Plice | 181/242 |
| 5,263,093 | A | * | 11/1993 | Nakamura et al. | 381/357 |
| 2005/0033188 | A1 | * | 2/2005 | Whitaker et al. | 600/490 |
| 2006/0093171 | A1 | | 5/2006 | Zhe et al. | |

FOREIGN PATENT DOCUMENTS

| | | |
|---|---|---|
| GB | 400 629 A | 10/1933 |
| JP | 06-014888 | 1/1994 |

OTHER PUBLICATIONS

Extended European Search Report, Application No. 07118514.4-1224/1915028;Dec. 23, 2010.

* cited by examiner

*Primary Examiner* — Ha Tran T Nguyen
*Assistant Examiner* — Raj R Gupta
(74) *Attorney, Agent, or Firm* — Merek, Blackmon & Voorhees, LLC

(57) ABSTRACT

The present invention provides a condenser microphone capable of detecting small sounds (e.g., Korotkoff sounds) with high sensitivity even in environments with variations in pressure, such as cuff pressure. A condenser microphone (10) is disposed as an acoustic sensor for detecting Korotkoff sounds in a communication space reachable by the internal pressure of the cuff of a blood pressure gauge. In the condenser microphone, a diaphragm (13) and a backplate 14) are disposed in the interior of a housing (11), an aeration hole (30) is formed in a wall (11B) that blocks off the housing back surface, and a sound-absorbing element (20) having sound absorption characteristics with respect to a frequency band targeted for detection is disposed on the front surface of a housing (11).

13 Claims, 7 Drawing Sheets

CONDENSER MICROPHONE, MICROPHONE UNIT, AND BLOOD PRESSURE GAUGE

BACKGROUND OF THE INVENTION

1. Field of the Invention

The present invention relates to a condenser microphone capable of detecting acoustic signals with high sensitivity under changing pressure conditions, to a microphone unit configured with the condenser microphone as the main component, and to a blood pressure gauge for measuring blood pressure by detecting Korotkoff sounds using the microphone.

2. Description of the Related Art

A blood pressure gauge that detects Korotkoff sounds using a microphone and calculates blood pressure values based thereon is conventionally known. Configurations are known such as one in which a microphone is disposed at an end portion of a conduit that communicates with a cuff to detect Korotkoff sounds carried through the air in the interior of a conduit (for example, see Japanese Patent Laid Open Publication No. 6-14888).

SUMMARY OF THE INVENTION

When a microphone is disposed at an end portion of a conduit that is in communication with a cuff, as described above, generally it is suggested that the microphone be disposed so as to contact the end wall of the conduit. However, noise can easily be picked up via the conduit wall, and in practice it is difficult to identify faint Korotkoff sounds.

In addition, it is suggested that the microphone be disposed directly at the end opening of the conduit. However, to measure blood pressure, the conduit communicating with the cuff must be kept airtight and the same pressure fluctuation as in the interior of a cuff is applied to the microphone. Therefore, it is believed difficult to use a condenser microphone that detects Korotkoff sounds by means of diaphragm vibration.

Taking note of the circumstances described above, an object of the present invention is to provide a condenser microphone capable of identifying and detecting faint sounds (such as Korotkoff sounds) with high sensitivity under an environment of fluctuating pressure, such as cuff pressure, to provide a microphone unit that uses this microphone as the main component, and to provide a blood pressure gauge that uses such microphones.

The condenser microphone of the present invention according to a first aspect comprises a condenser microphone in which a diaphragm and a backplate are disposed as two opposing electrodes inside a housing having an opening for admitting sound waves in a front surface, wherein an aeration hole is formed in a wall portion that blocks off a back surface of the housing, and a sound-absorbing filter having sound absorption characteristics with respect to a frequency band targeted for detection is disposed so as to cover the opening or aeration hole in one of the front surface or back surface of the housing.

The invention according a second aspect comprises the condenser microphone according to the first aspect, wherein a sound-absorbing element is affixed as the sound-absorbing filter to the front surface of the housing in a state in which an adhesive is placed on a periphery of the opening in the front surface of the housing.

The invention according to a third aspect comprises the condenser microphone according to the first aspect, wherein a breathable fabric element is affixed to the front surface of the housing in a state in which an adhesive is placed on a periphery of the opening in the front surface of the housing, and a sound-absorbing element is affixed as the sound-absorbing filter to an upper surface thereof via an adhesive.

The microphone unit of the present invention according to a fourth aspect comprises a microphone unit comprising the condenser microphone according to any of the first to third aspects as a main component thereof, wherein the condenser microphone is accommodated inside a unit case having a connection opening at a front end and an assembly opening on a back end in a state in which a front surface thereof faces the connection opening and a gap is maintained along a periphery of the housing; the opening in a back surface of the unit case is blocked off with a lid plate in a state in which a gap is maintained relative to the condenser microphone; two terminals of the condenser microphone are each allowed to extend to the outside from a through-hole formed in the lid plate; and a sealant is packed on an external surface of the lid plate to seal the gap between the lid plate and the unit case, as well as the gap between the lid plate and the terminals.

The invention according to a fifth aspect comprises the microphone unit according to the fourth aspect, wherein a single notch is created on a peripheral edge of the opening in the back surface of the unit case; a single projection is created on a peripheral edge of the lid plate; the notch and projection are aligned in position to fit the lid plate into the opening in the back surface of the unit case, thereby establishing a positional relationship between the two terminals of the condenser microphone and the unit case; and a configurational marking for distinguishing the two terminals is provided to an external surface of the unit case.

The invention according to a sixth aspect comprises the microphone unit according to the fourth or fifth aspect, wherein a nontransparent sealant having a color different from that of the unit case and lid plate is used as the sealant.

The blood pressure gauge of the present invention according to a seventh aspect comprises a blood pressure gauge comprising a cuff that is wound around a blood pressure measurement area; a pressurizing device for pressurizing the cuff; a depressurizing device for depressurizing the cuff; and an acoustic sensor for detecting the Korotkoff sounds transmitted through the air in the cuff, wherein the condenser microphone according to any of the first to third aspects is used as the acoustic sensor; and the condenser microphone is disposed in a communication space reachable by the internal pressure of the cuff.

The blood pressure gauge of the present invention according to an eighth aspect comprises a blood pressure gauge comprising a cuff that is wound around a blood pressure measurement area; a pressurizing device for pressurizing the cuff; a depressurizing device for depressurizing the cuff; a conduit communicating with the cuff; and an acoustic sensor for detecting the Korotkoff sounds transmitted through the air in the conduit, wherein the microphone unit according to any of the fourth to sixth aspects is used as the acoustic sensor, and the connection opening of the microphone unit is connected to an end portion of the conduit.

According to the invention of the first aspect, an aeration hole is provided in a wall that covers the back surface of the housing, making it possible to conduct pressure essentially equal to [that on] the front surface side also to the back surface side of the diaphragm. Therefore, it is possible to use [the present invention] as an acoustic sensor even under a pressure environment without imposing on a diaphragm a superfluous load due to fluctuation in pressure. In addition, since [the present invention] is configured to exclude sounds in a frequency band targeted for detection by using a sound-absorbing filter from air vibrations that are input to one or the other surface for receiving air vibrations that are input to both surfaces of the diaphragm, sound waves in the frequency band targeted for detection are admitted only from the other surface, with vibrations in other frequency bands canceling one another out in both surfaces. As a result, only electrical signals corresponding to sounds in the frequency band targeted for detection are output from the diaphragm and the backplate, making it possible to achieve high detection sensitivity when the microphone is used as an acoustic sensor.

In the invention according to the second aspect, since the opening of the front surface of the housing is not blocked by adhesive, air pressure can be input into the front surface of the diaphragm through a sound-absorbing element while sound waves in the frequency band targeted for detection are being absorbed by a sound-absorbing element.

In the invention according to the third aspect, a condenser microphone with high sensitivity can be configured simply by directly attaching a sound-absorbing element to a fabric element for preventing wind noise, even in the case of a conventionally available condenser microphone in which the fabric element is affixed to the front surface, making it possible to dispense with the time needed to peel off the fabric element.

In the invention according to the fourth aspect, it is possible to detect with high sensitivity sound carried through air within a pressure conduit while maintaining an airtight state, simply by airtightly communicating the connection opening of the unit case with the pressure conduit targeted for detection, for example.

In the invention according to the fifth aspect, the following effect is produced. In other words, as with the invention according to fourth aspect, when a small condenser microphone is accommodated in a case and the lid is replaced, it is difficult to discern which of two terminals is on the positive side and which is on the negative side. However, in the invention according to the fourth aspect, a configurational marking is attached to an outer surface of the unit case, making it easy to distinguish the two terminals from outside the unit case. Also, at the time when the terminals are passed via a through-hole in the lid plate, passing the terminals while ensuring that the terminals can be distinguished from each other allows the terminals to be automatically positioned based on projections and notches at the time when the lid plate is fitted into the unit case. Accordingly, assembly can be performed easily without mistaking positioning of the terminals.

In the invention according to the sixth aspect, a color of the sealant that fills the exterior surface of a lid plate is configured as a different non-transparent color from [that of] the unit case and the lid plate. Accordingly, it is possible to easily visually check whether or not the sealant has been left out.

In the invention according to the seventh aspect, a condenser microphone according to any of the first to third aspects is disposed in a communication space reachable by the inner pressure of the cuff. Accordingly, it is possible to detect Korotkoff sounds with high sensitivity without being affected by changes in the inner pressure of the cuff. In other words, a low-frequency component such as fluctuation in the inner pressure (including pulse pressure) of the cuff is cancelled out by acting on both surfaces of the diaphragm. Only high-frequency components such as Korotkoff sounds can be detected with high sensitivity by allowing pressure to be exerted upon one surface of a diaphragm.

In the invention according to the eighth aspect, the connection opening of the microphone unit according to any of the fourth through sixth aspects is connected to an end portion of a conduit that communicates with the cuff. Accordingly, it is possible, for example, to detect with high sensitivity Korotkoff sounds transmitted via a conduit (tube) for connecting a cuff with a pressurizing device and a depressurizing device without any effect from the changes in the inner pressure of the cuff. In other words, low-frequency components such as pressure fluctuations (including pulse pressure) within a cuff are cancelled out by acting on both surfaces of a diaphragm, and only high-frequency components such as Korotkoff sounds can be detected with high sensitivity since this component acts on one surface of a diaphragm. Also, since the conduit in this instance can be shared for both cuff pressure conduction and discharge and for Korotkoff sounds detection, excess conduit, wiring, and the like need not be provided.

BRIEF DESCRIPTION OF THE DRAWINGS

FIG. 4 is a block diagram of the microphone unit, wherein

FIG. 5 is an exploded view of the microphone unit, wherein

DESCRIPTION OF THE PREFERRED EMBODIMENTS

Embodiments of the present invention will now be described in reference to drawings.

Figure 1:
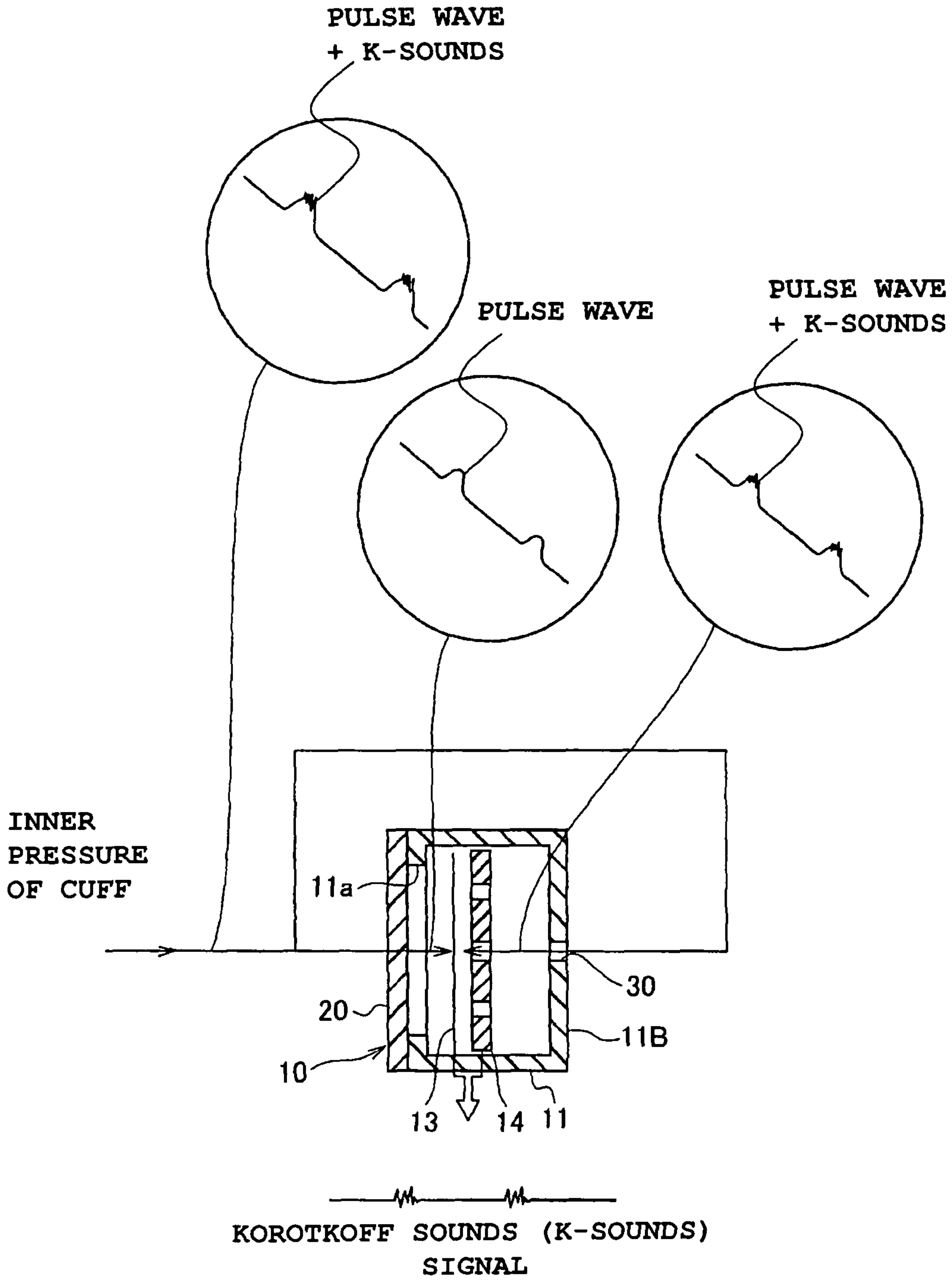
FIG. 1 is a view showing the general configuration of the condenser microphone according to an embodiment of the present invention.
Figure 2:
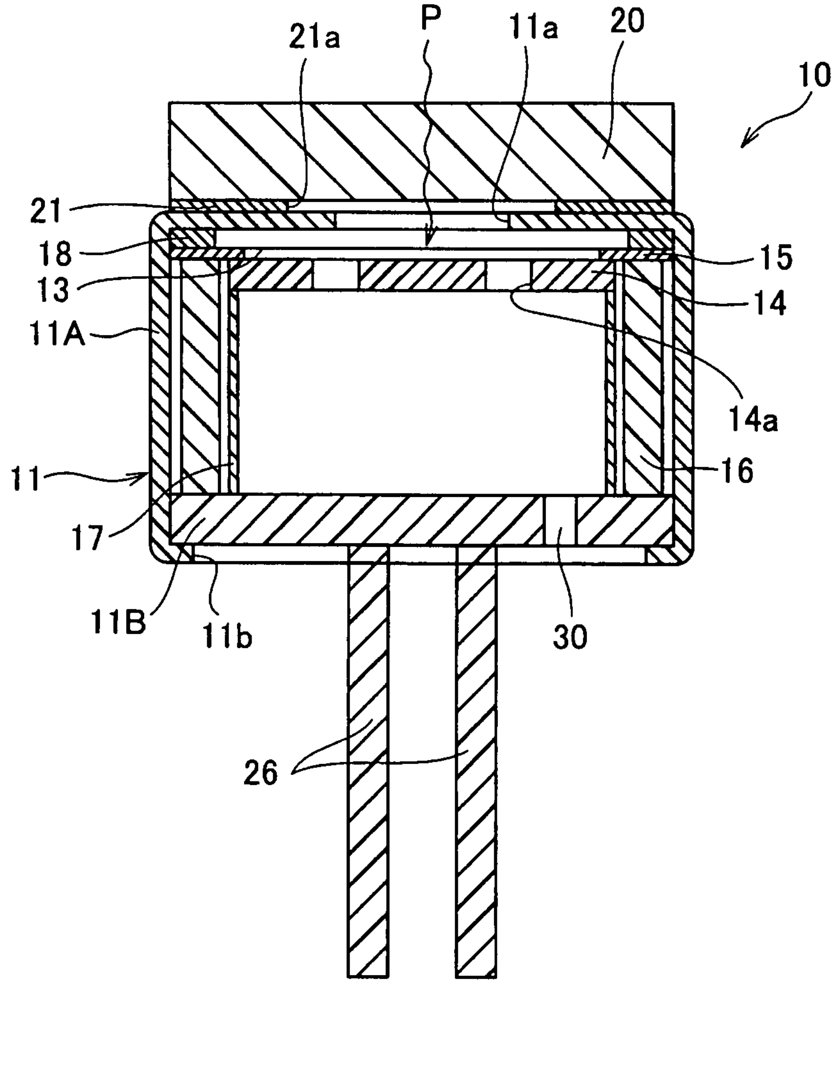
FIG. 2 is a cross section showing a specific configuration of the condenser microphone.
Figure 3:
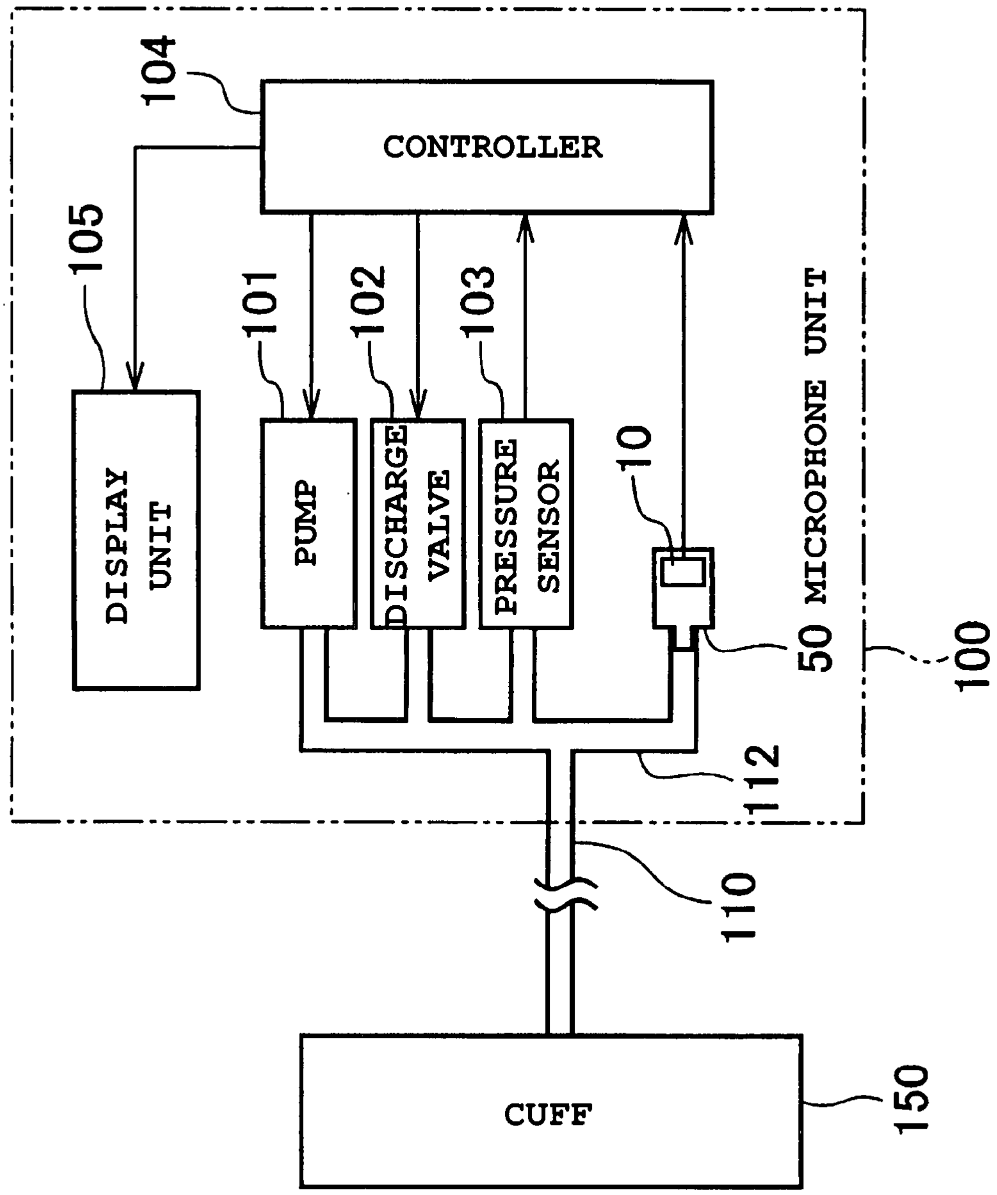
FIG. 3 is a schematic block diagram of a blood pressure gauge in which a microphone unit having the condenser microphone as a main component is used as an acoustic sensor for detecting Korotkoff sounds.
Figure 4A:
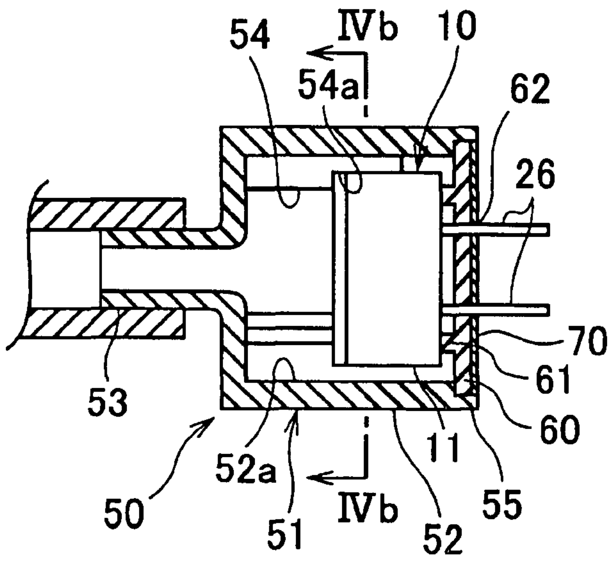
FIG. 4A is a longitudinal section and FIG. 4B is a cross section of IVb-IVb in FIG. 4A.
Figure 4B:
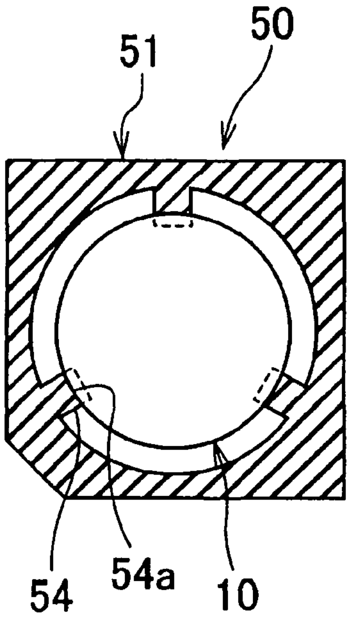
Figure 5A:
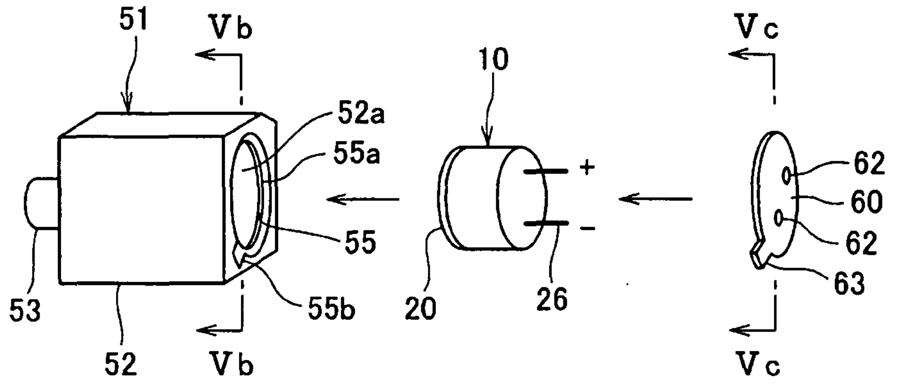
FIG. 5A is an exploded perspective view of the overall configuration.
Figure 5B:
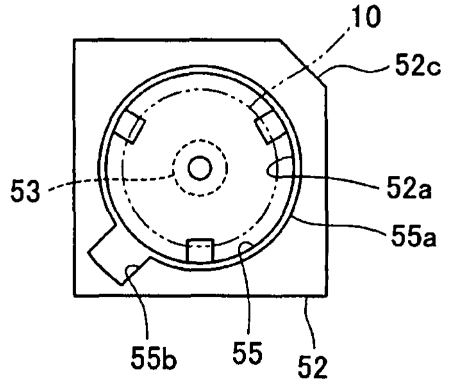
FIG. 5B is an arrow view of Vb-Vb in FIG. 5A.
Figure 5C:
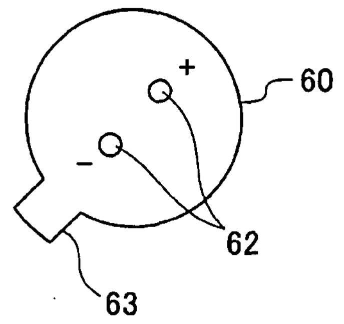
FIG. 5C is an arrow view of Vc-Vc in FIG. 5A.

FIG. 1 is a view showing the general configuration of the condenser microphone according to an embodiment of the present invention. FIG. 2 is a cross section showing a specific configuration of the condenser microphone. FIG. 3 is a schematic block diagram of a blood pressure gauge in which a microphone unit having the condenser microphone as a main component is used as an acoustic sensor for detecting Korotkoff sounds. FIG. 4 is a block diagram of the microphone unit, wherein FIG. 4A is a longitudinal section and FIG. 4B is a cross section of IVb-IVb in FIG. 4A. FIG. 5 is an exploded view of the microphone unit, wherein FIG. 5A is an exploded perspective view of the overall configuration, FIG. 5B is an arrow view of Vb-Vb in FIG. 5A, and FIG. 5C is an arrow view of Vc-Vc in FIG. 5A.

As shown in the general configuration in FIG. 1, a condenser microphone 10 in the embodiment comprises a condenser microphone in which a diaphragm 13 and a backplate 14 are disposed as two opposing electrodes inside a housing 11 having an opening 11*a* for admitting sound waves in a front surface, wherein an aeration hole 30 is formed in a wall portion 11B (substrate) that blocks off a back surface of the housing 11, and a sound-absorbing element 20 acting as a sound-absorbing filter that has sound absorption characteristics with respect to a frequency band targeted for detection is disposed so as to cover the opening 11*a* on the front surface of the housing 11.

When the aeration hole 30 is provided to the wall portion 11B that blocks off the back surface of the housing 11, as described above, it is possible to conduct essentially identical pressure both to the back surface side and to the front surface side of the diaphragm 13. Therefore, it is possible to use [this device] as an acoustic sensor without problem under a pressure environment and without imposing a superfluous load due to fluctuations in pressure on the diaphragm 13. Also, since [the device] is configured so that, of the air vibrations input to both surfaces of the diaphragm 13, sound in the frequency band targeted for detection is excluded from air vibration input to the front surface by the sound-absorbing element 20, sound waves in the frequency band targeted for detection are admitted only to the back surface, and vibrations in other frequency bands are mutually cancelled out on both surfaces. Ultimately, only electrical signals corresponding to sound in the frequency band targeted for detection are output from the diaphragm 13 and the backplate 14, making it possible to achieve a high level of detection sensitivity when the device is used as an acoustic sensor.

For example, as discussed below, when the condenser microphone 10 is disposed in an environment reachable by the inner pressure of the cuff of a blood pressure gauge, the inner pressure of the cuff operates on the front surface and the back surface of the diaphragm 13. However, since the sound-absorbing element 20, which has the property of absorbing sound waves in the frequency band of Korotkoff sounds (30 Hz to 150 Hz), is disposed on the front surface, air vibrations including Korotkoff sounds operate only on the back surface of the diaphragm 13. In other words, since the sound-absorbing element 20 fulfills the role of low-pass filter, low-frequency air vibrations (vibrations up to the pulse wave level) reach diaphragm 13, while high-frequency vibrations (Korotkoff sounds) are excluded from the front surface by the sound-absorbing element 20. Therefore, only the high-frequency signals (Korotkoff sounds, or K sound signal) remaining after the low-frequencies cancel each other out are detected from the condenser microphone 10.

A specific configuration will now be described using FIG. 2. The housing 11 comprises a conical metallic casing 11A, which has round openings 11*a* and 11*b* on the front surface and back surface, and a printed substrate (wall portion) 11B disposed so as to block off the opening 11*b* on the back surface of the casing 11A. The housing 11 accommodates, starting from the front side, the diaphragm (vibrating membrane) 13 and the backplate (fixed electrode) 14 having a hole 14*a*. Rings 16, 17, and 18, and a cushioning plate 15 are provided in order to support the diaphragm and the backplate. In addition, two positive and negative terminals 26 linked to the diaphragm 13 and the backplate 14 extend on the external surface side of the printed substrate 11B.

Also, the sound-absorbing element 20 composed of urethane foam or the like is affixed to the front surface of the casing 11A in a state in which an adhesive 21 is placed on the perimeter of the opening 11*a*. Therefore, the pressure (air vibration) P in the cuff passes through the sound-absorbing element 20 as well as through a round hole 21*a* in the adhesive 21 and the opening 11*a* in the casing 11A, and is admitted to the front surface of the diaphragm 13. In addition, the pressure (air vibration) P in the cuff operates directly on the back surface of the diaphragm 13 through the aeration hole 30 provided in the substrate 11B and the through-hole 14*a* of the backplate 14.

Following is a description of a microphone unit equipped with the condenser microphone, and a blood pressure gauge to which the unit is applied.

As shown in FIG. 3, the blood pressure gauge comprises a cuff (vascular pressure compression sleeve with an air pocket) 150 wrapped around a blood pressure measurement area, a pressurizing device (pump) 101 for pressurizing the cuff 150, a depressurizing device (discharge valve) 102 for depressurizing the cuff 150, a pressure sensor 103 for detecting the pressure of the cuff 150, conduits 110 and 112 for communicating with the cuff 150, a microphone unit 50 as an acoustic sensor for detecting Korotkoff sounds carried through the air inside the conduits 110 and 112, a controller 104 for performing overall control of blood pressure measurements, a display unit 105 for displaying measurement results, and the like.

Elements other than the cuff 150 are included within the blood pressure gauge main unit 100. The cuff 150 and the blood pressure gauge main unit 100 are connected by a tube (duct), which is a conduit 110. The microphone unit 50 is connected to an end portion of the conduit 112 inside the blood pressure gauge main unit 100.

As shown in FIG. 4, the microphone unit 50 is configured so that the above-described condenser microphone 10, in a state in which the front surface is oriented toward a connection opening 53 and a gap is maintained around the perimeter of the housing 11, is accommodated in the interior of a round holding chamber 52*a* in a unit case 51 that has a connection opening 53 at a front end thereof and an assembly opening 55 at the back surface of a main unit 52 shaped as a rectangular column. The opening 55 in the back surface of the unit case 51 is covered by a lid plate 60 in a state in which a gap is maintained with the condenser microphone unit 10; the two terminals 26 of the condenser microphone 10 extend to the outside from through-hole 62 formed in the lid plate 60; and the exterior surface of the lid plate 60 is packed with a sealant (adhesive or the like) 70 to seal the gap between the lid plate 60 and the unit case 51 and the gap between the lid plate 60 and the terminals 26.

In order to maintain the gap, a support projection 54 with shoulders 54*a* at three locations is provided, with space opened peripherally, along the interior perimeter wall of the round holding chamber 52*a*, and a holddown protrusion 61 is provided to the inner surface of the lid plate 60. In addition, a perimeter groove 55*a* into which the round lid plate 60 fits is formed on the perimeter of the assembly opening 55, and a notch 55*b* is provided at a single location on this perimeter groove 55. The condenser microphone 10 is held without any backlash in the interior of the unit housing 52 in a state in which a gap is maintained by pressing the front end of the housing 11 against the shoulders 54*a* of the support protrusion 54 and pressing down the back end surface of the housing 11 by the holddown protrusion 61 of the lid plate 60.

In addition, a positioning projection 63 that fits into the notch 55*b* is provided on the perimeter edge of the lid plate 60. As shown in FIGS. 5B and 5C, the notch 55*b* and the projection 63 are provided at a location at which the two through-holes 62 for passing the terminals 26 are distinguished from each other. For example, the projection 63 is provided at a location close to the through-hole 62 for the negative terminal, while the notch 55*b* is provided at a location near one of the corners of the main unit 52 shaped as a rectangular column in the unit case 51. A mounting 52*c* is provided as a configurational marking on the opposite corner. In addition, the lid plate 60 is fitted into the perimeter groove 55*a* of the opening 55 of the back surface of the unit case 51 by aligning the notch 55*b* and the projection 63.

Also, a non-transparent sealant having a color different from that of the unit case 51 and the lid plate 60 is used as the sealant 70 packed on the top of the lid plate 60. For instance, a white, black, green, red, or other non-transparent color sealant 70 is used in cases in which the unit case 51 and the lid plate 60 are composed of transparent resin.

When the microphone unit 50 thus configured is used, it is possible to detect with high sensitivity Korotkoff sounds carried through the air inside the cuff 150, while maintaining an airtight state, simply by airtightly connecting the connection opening 53 of the unit case 51 to the end opening of the conduit 112 targeted for detection, as shown in FIG. 3.

In addition, as shown in FIG. 4, when the compact condenser microphone 10 is accommodated in the unit case 51 and closed by the lid plate 60, it becomes difficult to distinguish which of the two terminals 26 is on the positive or negative side. However, since a configurational marking (mounting 52*c*) is provided on the outer surface of the unit case 51, it is possible to easily distinguish the two terminals 26 from outside the unit case 51. Also, passing the terminals 26 via the through-hole 62 in the lid plate 60 while allowing the terminals 26 to be distinguished from each other at the time when the terminals 26 are passed through the hole allows alignment to be automatically performed using the projection 63 and the notch 55*b* at the time when the lid plate 60 is fitted onto the unit case 51, and assembly can therefore be performed easily without mistaking the positioning of the terminals 26.

In addition, the color of the sealant 70 on the exterior surface of the lid plate 60 is a non-transparent color different from that of the unit case 51 and the lid plate 60, making it possible to easily check visually whether or not the sealant 70 has been accidentally left out.

Also, the blood pressure gauge is configured so that the connection opening 53 of the above-described microphone unit 10 is connected to an end portion of the conduit 112 for communicating with the cuff 150. Therefore, it is possible to detect with high sensitivity Korotkoff sounds transmitted via the conduits 110 and 112 without any effect from the changes in the inner pressure of the cuff 150. In other words, low-frequency components such as pressure fluctuations (including pulse pressure) within the cuff 150 act upon both surfaces of the diaphragm 13, and are thereby canceled out. Only high-frequency components such as Korotkoff sounds act upon one side of the diaphragm 13, and can thereby be detected with high sensitivity. In addition, the conduit 110 can be shared both for the introduction and discharge of cuff pressure and for detection of Korotkoff sounds, making it possible to dispense with excess conduit, wiring, and the like and to optimize handling and costs.

Figure 6:
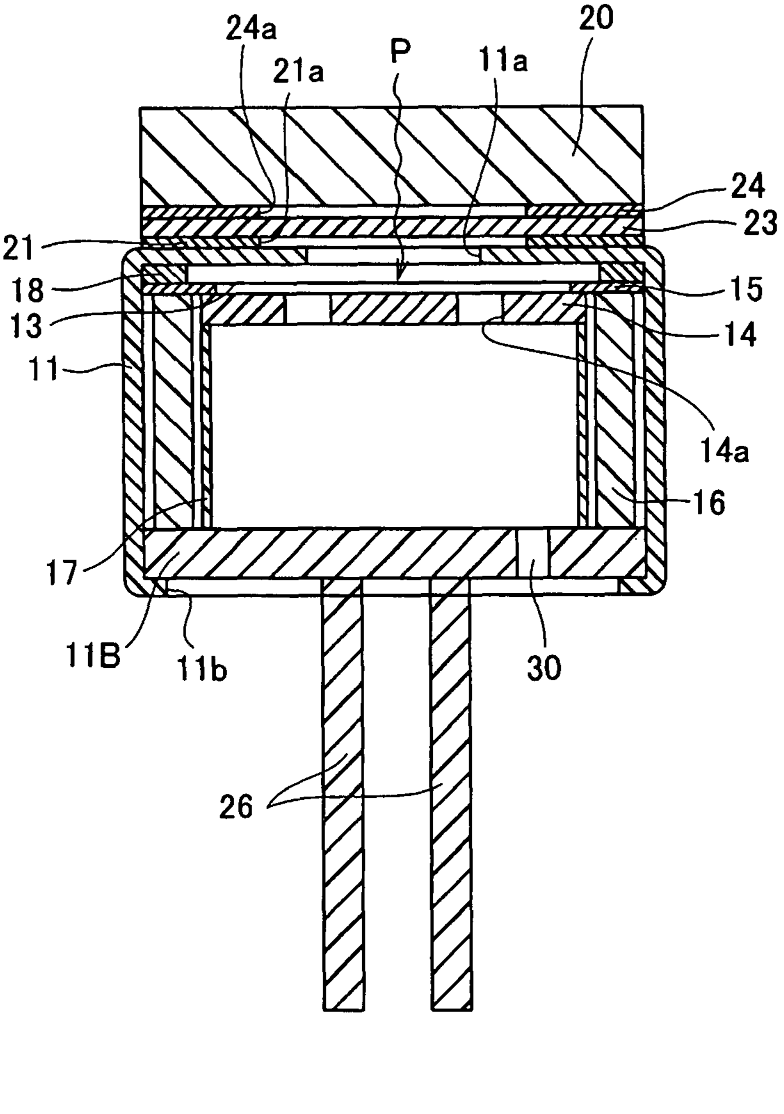
FIG. 6 is a cross section showing the configuration of a condenser microphone according to another embodiment of the present invention.
Figure 7:
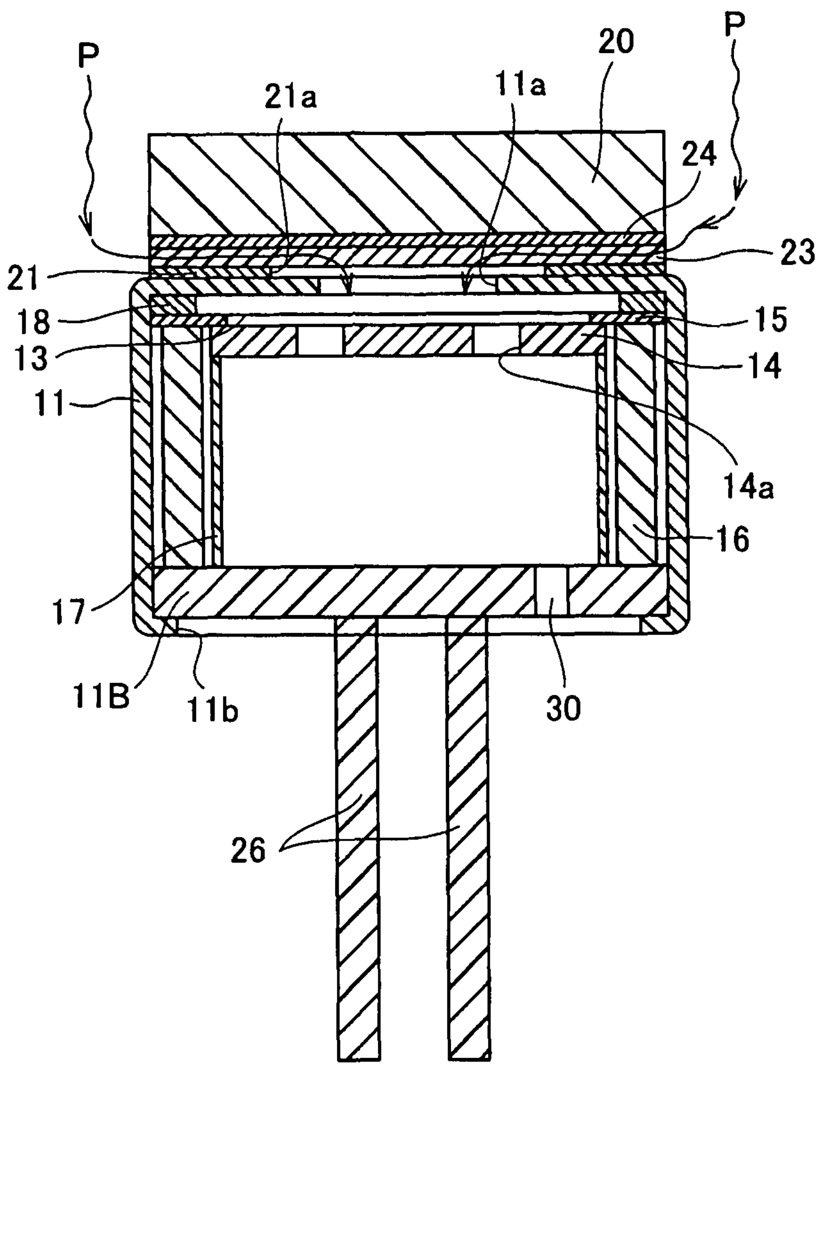
FIG. 7 is a cross section showing the configuration of a condenser microphone according to yet another embodiment of the present invention.

As shown in FIGS. 6 and 7, when a breathable fabric element 23 is affixed in a state in which adhesive 21 is applied to the perimeter of the front surface opening 11*a* on the front surface of the housing 11, the sound-absorbing element 20 may be affixed as a sound-absorbing filter to the top surface thereof by an adhesive 24.

The example in FIG. 6 shows a case in which the adhesive 24 is disposed so that a round center hole 24*a* is left open. The example in FIG. 7 shows a case in which the adhesive 24 is disposed over the entire inner surface of the sound-absorbing element 20. In the case of FIG. 6, the round center hole 24*a* is opened in the adhesive 24, and the pressure P in the cuff can operate upon the interior through the sound-absorbing element 20. In the case of FIG. 7, however, the pressure P in the cuff can operate through an interior gap in the thickness direction of the fabric element 23. In this instance, sound waves in the high-frequency range are damped when air vibrations pass through the interior gap in the thickness direction of the fabric element 23. Accordingly, the fabric element 23 as such partially fulfills the role of a sound-absorbing filter. Therefore, a subsequently affixed component need not necessarily be the sound-absorbing element 20.

In either case, even a commercially available condenser microphone in which a fabric element 23 for wind noise prevention is affixed to the front surface can be configured as a condenser microphone provided with high sensitivity simply by attaching a sound-absorbing element 20 over the fabric element 23 without modification, and the extra work involved in peeling off the fabric element 23 can be dispensed with.

In addition, the embodiment described above shows a case in which the sound-absorbing element 20 is disposed on the front surface of the housing 11. However, the sound-absorbing element 20 may also be disposed so as to cover the aeration hole 30 on the back surface of the housing 11.

Also, the embodiment described above shows a case in which the condenser microphone 10 is connected to an end portion of the conduit 112 in the form of the microphone unit 50. However, the condenser microphone 10 may be disposed directly in a communication space reachable by the inner pressure of the cuff 150.

In addition, the embodiment described above shows a case in which the condenser microphone 10 is applied to a blood pressure gauge as an acoustic sensor for detecting Korotkoff sounds. However, the condenser microphone of the present invention can also be used as a microphone for an electronic hearing aid and as a microphone for other applications.

What is claimed is:

1. A condenser microphone in which a diaphragm and a backplate are disposed as two opposing electrodes inside a housing having an opening for admitting sound waves in a front surface, wherein an aeration hole is formed in a wall portion that blocks off a back surface of said housing; and a sound-absorbing filter having sound absorption characteristics with respect to a frequency band targeted for detection is disposed so as to entirely cover said opening or aeration hole in one of the front surface or back surface of said housing when the sound waves are admitted on a front surface and back surface of the housing, air vibrations of the frequency band targeted for detection are being cut on a surface of the diaphragm on a side that the sound-absorbing filter is disposed, while the air vibrations of the frequency band targeted for detection are not being cut on a surface of the diaphragm on a side that the sound-absorbing filter is not disposed; and air vibrations on the surfaces of the diaphragm other than air vibrations of the frequency band targeted for detection are canceled out, to thereby detect the air vibrations of the frequency band targeted for detection.

2. A blood pressure gauge comprising:

a cuff that is wound around a blood pressure measurement area;

a pressurizing device for pressurizing said cuff;

a depressurizing device for depressurizing said cuff; and an acoustic sensor for detecting the Korotkoff sounds transmitted through the air in said cuff, wherein the condenser microphone according to claim 1 is used as said acoustic sensor; and said condenser microphone is disposed inside a communication space reachable by the internal pressure of said cuff.

3. The condenser microphone according to claim 1, wherein a sound-absorbing element is affixed as said sound-absorbing filter to the front surface of said housing in a state in which an adhesive is placed on a periphery of the opening in the front surface of said housing.

4. A microphone unit comprising the condenser microphone according to claim 3 as a main component thereof, wherein said condenser microphone is accommodated inside a unit case having a connection opening at a front end and an assembly opening on a back end in a state in which a front surface thereof faces said connection opening and a gap is maintained along a periphery of said housing;

the opening in a back surface of said unit case is blocked off with a lid plate in a state in which a gap is maintained relative to said condenser microphone; two terminals of said condenser microphone are each allowed to extend to the outside from a through-hole formed in said lid plate; and a sealant is packed on an external surface of the lid plate to seal the gap between the lid plate and the unit case, as well as the gap between the lid plate and the terminals.

5. The microphone unit according to claim 4, wherein a nontransparent sealant having a color different from that of said unit case and lid plate is used as said sealant.

6. The condenser microphone according to claim 1, wherein a breathable fabric element is affixed to the front surface of said housing in a state in which an adhesive is placed on a periphery of the opening in the front surface of said housing; and a sound-absorbing element is affixed as said sound-absorbing filter to an upper surface thereof via an adhesive.

7. A microphone unit comprising the condenser microphone according to claim 6 as a main component thereof, wherein said condenser microphone is accommodated inside a unit case having a connection opening at a front end and an assembly opening on a back end in a state in which a front surface thereof faces said connection opening and a gap is maintained along a periphery of said housing;

the opening in a back surface of said unit case is blocked off with a lid plate in a state in which a gap is maintained relative to said condenser microphone;

two terminals of said condenser microphone are each allowed to extend to the outside from a through-hole formed in said lid plate; and a sealant is packed on an external surface of the lid plate to seal the gap between the lid plate and the unit case, as well as the gap between the lid plate and the terminals.

8. The microphone unit according to claim 7, wherein a nontransparent sealant having a color different from that of said unit case and lid plate is used as said sealant.

9. A microphone unit comprising the condenser microphone according to claim 1 as a main component thereof, wherein said condenser microphone is accommodated inside a unit case having a connection opening at a front end and an assembly opening on a back end in a state in which a front surface thereof faces said connection opening and a gap is maintained along a periphery of said housing;

the opening in a back surface of said unit case is blocked off with a lid plate in a state in which a gap is maintained relative to said condenser microphone;

two terminals of said condenser microphone are each allowed to extend to the outside from a through-hole formed in said lid plate; and a sealant is packed on an external surface of the lid plate to seal the gap between the lid plate and the unit case, as well as the gap between the lid plate and the terminals.

10. The microphone unit according to claim 9, wherein a nontransparent sealant having a color different from that of said unit case and lid plate is used as said sealant.

11. A blood pressure gauge comprising:

a cuff that is wound around a blood pressure measure area;

a pressurizing device for depressurizing said cuff;

a conduit for communicating with said cuff; and an acoustic sensor for detecting the Korotkoff sounds transmitted through the air in said conduit, wherein the microphone unit according to claim 9 is used as said acoustic sensor; and the connection opening of said microphone unit is connected to an end portion of said conduit.

12. The microphone unit according to claim 9, wherein a single notch is created on a peripheral edge of the opening in the back surface of said unit case;

a single projection is created on a peripheral edge of said lid plate;

said notch and projection are aligned in a position to fit the lid plate into the opening in the back surface of the unit case, thereby establishing a positional relationship between the two terminals of said condenser microphone and the unit case; and a configurational marking for distinguishing said two terminals is provided to an external surface of said unit case.

13. The microphone unit according to claim 12, wherein a nontransparent sealant having a color different from that of said unit case and lid plate is used as said sealant.

* * * * *